United States Patent [19]

Vanderbel

[11] Patent Number: 4,975,810
[45] Date of Patent: Dec. 4, 1990

[54] LIGHT SOURCE

[75] Inventor: Frans G. Vanderbel, Southbridge, Mass.

[73] Assignee: Instrument Research Corporation, Southbridge, Mass.

[21] Appl. No.: 493,489

[22] Filed: Mar. 14, 1990

[51] Int. Cl.$^5$ ............................................. F21V 7/04
[52] U.S. Cl. ...................................... 362/32; 362/20; 362/232; 362/250; 362/254; 362/373; 362/802
[58] Field of Search ............... 362/254, 250, 32, 294, 362/373, 345, 207, 804, 20, 802, 184, 227, 232; 353/87

[56] References Cited

U.S. PATENT DOCUMENTS

| | | | |
|---|---|---|---|
| 3,265,881 | 8/1966 | Hovnanian et al. | 362/32 |
| 3,683,167 | 8/1972 | Rishton | 362/32 |
| 3,775,606 | 11/1973 | Bazell et al. | 362/32 |
| 4,410,929 | 10/1983 | Feinbloom et al. | 362/32 |

Primary Examiner—James C. Yeung
Attorney, Agent, or Firm—Norman S. Blodgett; Gerry A. Blodgett

[57] ABSTRACT

Light source for providing light to fibre optic medical instruments and the like, source including dual lamps for alternate use and an efficient cooling system.

7 Claims, 2 Drawing Sheets

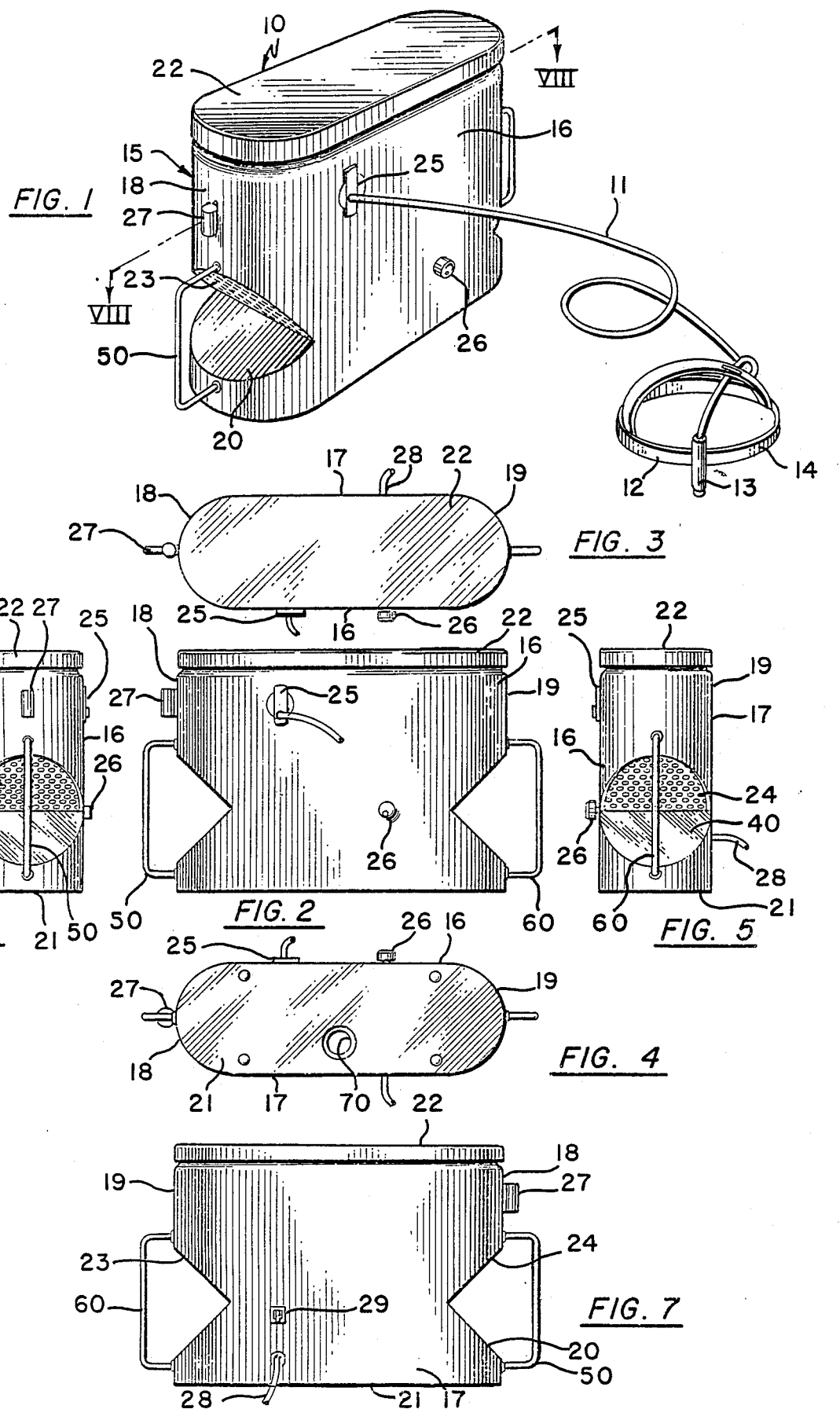

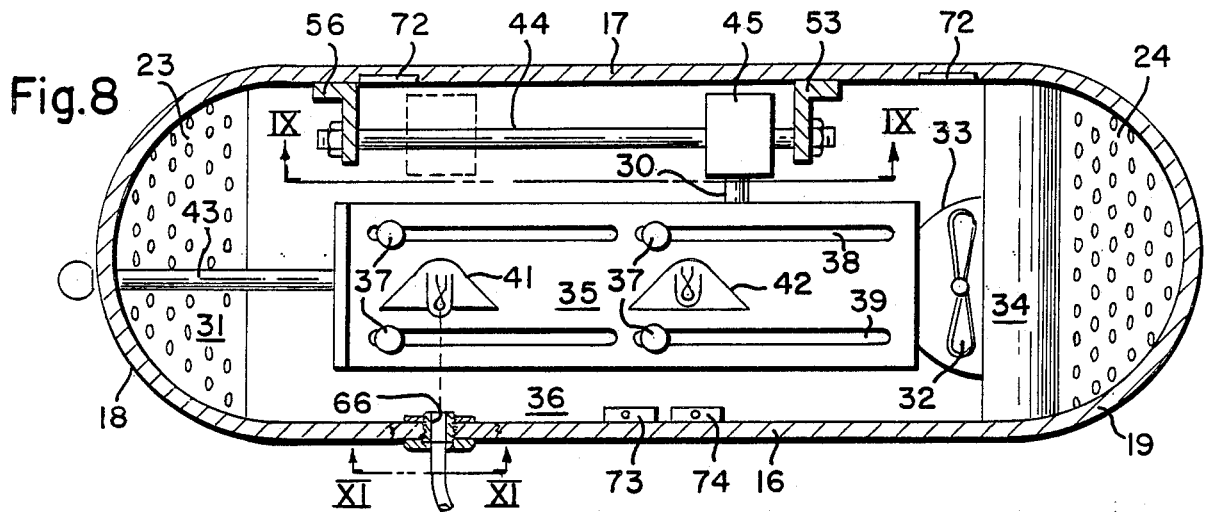
Fig.8
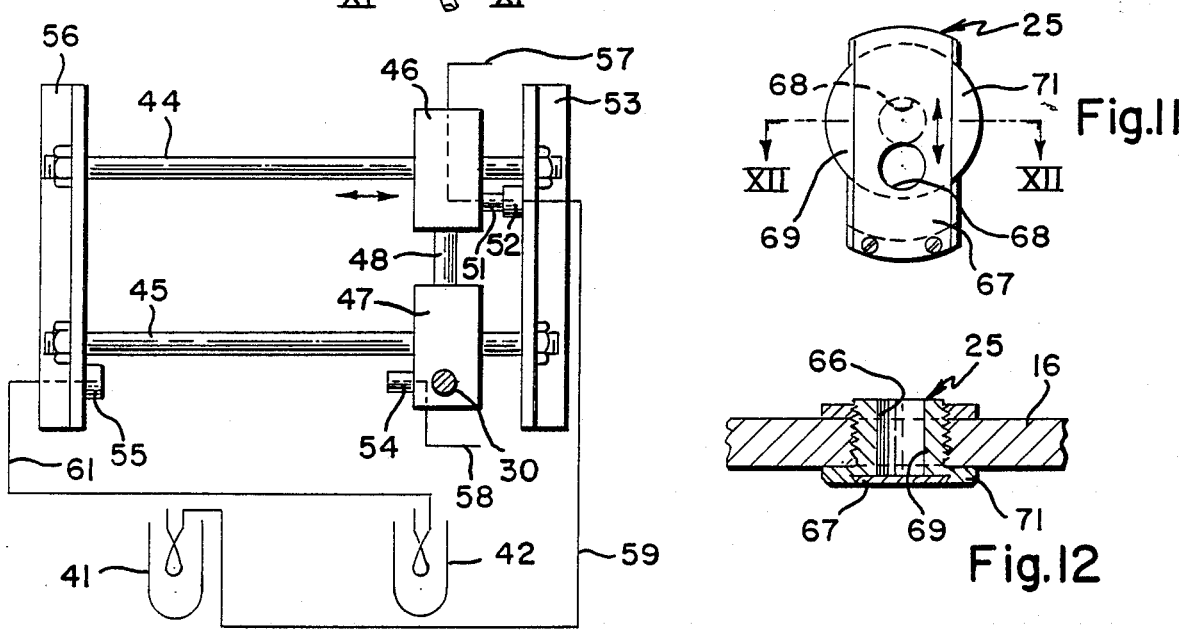
Fig.9
Fig.11
Fig.12
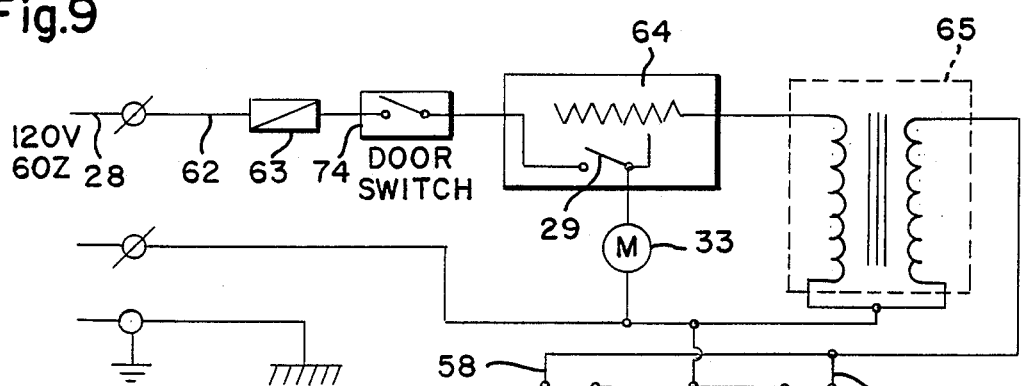
Fig.10
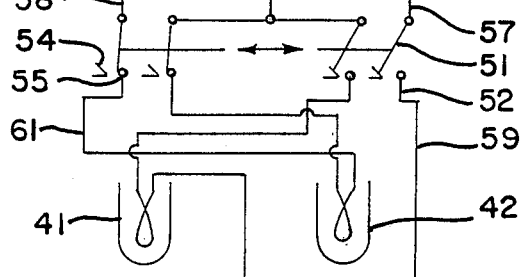

LIGHT SOURCE

BACKGROUND OF THE INVENTION

In providing light for a medical instrument, such as a headlight for use during surgery, it is very important that the supply of light not be interrupted for any substantial length of time In order to accomplish this function, it is necessary that the lamp emitting the light be free of conditions that can cause lamp failure. At the same time, provision must be made that a replacement lamp can be moved quickly into place and be immediately operative. Apparatus of this type have, in the past, been subject to erratic operation because of accidental blockage of the cooling system and because of the time required to replace a burned-out lamp. Additionally, prior art lamp sources have been difficult to move from place-to-place, due to the housing, and lamp being too hot to handle. These problems have been particularly troublesome in the tense atmosphere of the operating room. Furthermore, lamps cannot be changed by operating room personnel, because they need to remain "sterile" during the operating procedure. These and other difficulties experienced with the prior art devices have been obviated in a novel manner by the present invention.

It is, therefore, an outstanding object of the present invention to provide a light source providing for rapid replacement of an inoperative lamp.

Another object of the invention is to provide a light source having a self-operating shutter for a light-emitting aperture.

A further object of the invention is to provide a light source using dual lamps that can be readily used interchangeably.

Another object of the invention is to provide a light source having an effective cooling system whose air entrance and exit openings are protected against blockage.

A further object of the invention is to provide a light source having handles that remain cool even when the housing is very warm.

Another object of the invention is to provide a light source that is simple and rugged in construction, which is relatively inexpensive to manufacture, and which is capable of a long life of useful service with a minimum of maintenance.

SUMMARY OF THE INVENTION

In general, the invention has to do with a light source having a box-like housing with a front wall and two opposed second walls, defining an interior space and a venting screen on each of the said end walls. A fan is mounted in the internal space to provide for air flow through the venting screens and a lamp assembly is mounted in the interior space. A connector is mounted on one of the said walls for engagement with a fibre optic cable. More specifically, the connector includes a shutter to close an aperture when it is not connected to a fibre optic cable. The lamp assembly includes two lamps and a means for moving the lamps from a first position in which one lamp is in alignment with the connector to a second position in which the other lamp is in alignment with the connector. Furthermore, each end wall of the housing is provided with an indentation on the surface of which is located the said venting screen. A handle bar extends across each indentation to facilitate the carrying of the housing and to prevent the venting screens from becoming blocked.

BRIEF DESCRIPTION OF THE DRAWINGS

The character of the invention, however, may be best understood by reference to various specific structural forms, as illustrated by the accompanying drawings in which:

FIG. 1 is a perspective view of a light source embodying the principles of the present invention and shown in use with a fibre optic cable leading to a surgical headlight, FIG. 2 is a front elevational view of the light source, FIGS. 3, 4, 5, 6 and 7 are top plan, bottom plan, right side elevational, left side elevational, and rear elevational view, respectively, of the light source, FIG. 8 is a horizontal sectional view of the light source, taken on the line V—V of FIG. 1, FIG. 9 is a vertical sectional view of the light source, taken on the line IX—IX of FIG. 8, FIG. 10, is a schematic view of the electrical circuitry of the light source, FIG. 11 is an enlarged front elevational view of a fibre optic connector forming part of the light source taken on the line XI—XI of FIG. 8, and FIG. 12 is a horizontal sectional view of the connector taken on the line XII—XII of FIG. 11

DESCRIPTION OF THE PREFERRED EMBODIMENT

Referring first to FIG. 1, which best shows the general features of the invention, the light source, indicated generally by the reference number 10, is shown in use with a fibre optic cable 11 leading to medical apparatus, such as a surgical headlight 12. The headlight has a light-directing element 13 adjustably mounted on a headband 14.

FIGS. 1 through 7 illustrate the exterior configuration of the light source. It includes a box-like housing 15 having a front wall 16, a rear wall 17, and two opposed end walls 18 and 19. These walls are integrally combined with a bottom wall 21 to form an enclosure with an open end that is closed by a hinged cover 22. The six above-named walls define an interior space.

A venting screen 23 is provided on the end wall 18, while a similar venting screen 24 is mounted on the end wall 19. The end wall 18 is formed with a recess 20 whose surface carries the venting screen 23, which a similar recess 40 formed in the other end wall 19, carries the venting screen 24. Handles 50 and 60 bracket the recesses 20 and 40, respectively. A connector 25 is provided on the front wall 16 for engagement with the fiber optic cable 11. A rheostat knob 26 is also mounted on the front wall. An operating handle 27 is mounted on the end wall 18. An electrical cable 28 extends from the rear wall 17 and is adapted to be plugged into a 120 v. AC wall socket (not shown). In addition, the rear wall carries a main switch 29 (see FIG. 7).

FIG. 8 illustrates the contents of the interior space 31 formed by the front wall 16, the rear wall 17, and the end walls 18 and 19. A fan 32 driven by an electric motor 33 is mounted at one end of the elongated interior space and serves to draw air into the housing through the venting screen 24. A curved baffle 34 directs the air horizontally along the length of the housing.

A platform 35 is slidable lengthwise of the housing on a fixed horizontal wall 36 that is integrally opposed end walls 18 and 19. These walls are integrally combined with a bottom wall 21 to form an enclosure with an open end that is closed by a hinged cover 22. The six above-named walls define an interior space.

A venting screen 23 is provided on the end wall 18, while a similar venting screen 24 is mounted on the end wall 19. The end wall 18 is formed with a recess 20 whose surface carries the venting screen 23, which a similar recess 40 formed in the other end wall 19, carries the venting screen 24. Handles 50 and 60 bracket the recesses 20 and 40, respectively. A connector 25 is provided on the front wall 16 for engagement with the fiber optic cable 11. A rheostat knob 26 is also mounted on the front wall. An operating handle 27 is mounted on the end wall 18. An electrical cable 28 extends from the rear wall 17 and is adapted to be plugged into a 120 v. AC wall socket (not shown). In addition, the rear wall carries a main switch 29 (see FIG. 7).

FIG. 8 illustrates the contents of the interior space 31 formed by the front wall 16, the rear wall 17, and the end walls 18 and 19. A fan 32 driven by an electric motor 33 is mounted at one end of the elongated interior space and serves to draw air into the housing through the venting screen 24. A curved baffle 34 directs the air horizontally along the length of the housing.

A platform 35 is slidable lengthwise of the housing on a fixed horizontal wall 36 that is integrally formed in the housing and extends across it. The wall 36 is provided with pins 37 that extend through space, parallel, longitudinal slots 38 and 39 extending through the platform 35. Mounted on the platform 35 are two spaced incandescent lamps 41 and 42 having reflectors to direct light from the lamps toward the front wall 16. A rod 43 is fastened at one end to the movable platform 35, extends through the end wall 18, and is provided at the other end with the knob or handle 27. The rod 43 is provided with a flat vertical surface which carries warning indicia that is exposed when in the outer position.

FIGS. 8 and 9 show that a parallel vertically-spaced pair of bars 44 and 45 are mounted on the back wall 17 in parallel spaced relationship thereto. A pair of blocks 46 and 47 are slidably carried on the bars 44 and 45, respectively and are joined by a mechanical connector 48, so that they move together. The block 47 is joined to the platform 35 by a connecting rod 30, so that movement of the rod 43 serves to move the platform 35, the lamps 41 and 42, and the blocks 46 and 47 together lengthwise of the housing.

The block 46 is provided with a male electrical contact 51 extending toward a female electrical contact 52 fixedly mounted on a support 53 for the bars 44 and 45; the lower block 47 is, similarly, provided with a male electrical contact 54 directed toward a female electrical contact 55 carried on another support 56 for the bars.

An electrical lead 57 is connected through the upper block 46 to the contact 51, while a similar electrical lead 58 passes through the lower block 47 to the contact 54. An electrical lead 59 extends from the female connector 52 to the lamp 42, while an electrical lead 81 connects the female contact 55 to the lamp 41.

The electrical schematic shown in FIG. 10 illustrated the manner in which the lamps 41 and 42 and the fan motor 33 are supplied with electrical power. A line 62 forming part of the power cable 28 is connected to a 120 v. 60 H2. source and through a fuse 63, the main switch 29, and a rheostat 64 (controlled by the knob 26 of FIG. 1) to the primary coil of a transformer 65, the secondary coil of which is connected to the leads 57 and 58 which are joined to the male contacts 51 and 54, respectively. The female contacts 52 and 55 are connected through the lines 59 and 61 to the lamps 41 and 42, respectively.

Referring again to FIG. 8, it can be seen that the cover 22 is mounted on the housing 15 by means of hinges 72 at the top edge of the rear wall 17. At the front wall 16, the cover is held by a lock 73 and contacts a main switch 74.

FIGS. 11 and 12 show the details of the connector 25. The front wall 16 of the housing 15 is provided with an aperture 66 which is aligned with one of the lamps 41 or 42. A shutter 67 is slidable vertically from a lower position (as shown) to an upper position in which an aperture 68 is aligned with an aperture 69 and the aperture 67. The shutter has a dove-tailed cross-section permitting it to be guided by and slidable with a conforming guide 71. This structure prevents the user from harmful light rays produced by lamps 41 or 42, when the unit is in use.

The operation and advantages of the invention will now be readily understood in the light of the above description. During use, the light source 10 can be carried at the upper end of a vertical shaft forming part of a floor stand (not shown). The shaft extends into the bore 70 entering the bottom wall 21 and the light source is held in this manner at a selected vertical level.

The fibre optic cable 11 is introduced into the housing 15 and held in place by the connector 25. When the cable 11 is not so connected, the shutter 67 remains in the lower position and the aperture 68 is out of alignment with the aperture 66. The glare from the lamp does not, therefore, leave the housing. To connect the cable 11, therefore, it is necessary to lift the shutter 67 into its upper position where the aperture 68 is in alignment with the aperture 66. Light from the lamp is then free to exit into the cable 11 and pass to the headlight 12 and to the element 13.

To energize one of the lamps 41 or 42, it is only necessary to plug the electrical cable 28 into a wall socket and to operate the main switch 29. The transformer 65 operates to reduce the voltage to the lower valve needed for the lamps 41 and 42. Assuming that the apparatus is in the condition shown in FIG. 8 (with the lamp 41 in alignment with the aperture 66), the male contact 51 is in engagement with the female contact 52 and the electrical current passes through the line 56 to the lamp 41. This energizes the lamp 41 only and the light emitted passes to the aperture 66 for passage through the cable 11 to the headlight 12.

If the lamp 41 fails, it is only necessary to pull the rod 43 (by means of the handle 27) to the left to the extreme position shown in dotted lines in FIG. 8. This draws the platform 35 to the left, thus moving the lamp 41 away from alignment with the aperture 66 and moving the lamp 42 into alignment with the aperture. The movement of the platform serves to move the blocks 46 and 47 to the left on the rods 44 and 45, respectively, by virtue of a connecting rod 30 that joins the platform to the block 47. During this movement of the platform, the male contact 51 on the block 46 leaves the female contact 52; at the end of the travel to the left, the male contact 54 on the block 47 eventually engages to female contact 55. Electrical energy is then supplied to the lamp 42 and the light passes to the headlight. At the same time, the extended handle 27 will show a printed reminder to the user to replace or check the lamp in question. The handle cannot be pushed back, until the user disengages a blocking device.

The actuation of the main switch 29 also causes the fan motor 33 to be energized to operate the fan 32. Cooling air enters the housing 15 through the venting screen 24, passes upwardly through the fan 32 and is guided in the horizontal direction by the baffle 34. The air, therefore, is caused to flow over and around the platform 35 and the lamps 41 and 42, thus removing the heat generated by the lamps. After cooling the lamps, the air passes downwardly and out of the housing through the venting screen 23. The handles 50 and 60 serve a dual purpose; first of all, they extend well away from the housing, so that two hands can be used to move the light source. In this way, the source is supported securely against being dropped during transportation and, if the housing is somewhat hot from the lamp, there is no discomfort to the person moving the equipment. The flow of air over the handles (as well as their remote location from the housing) assures that they remain cool. At the same time, since the central vertical portion of each handle is located well away from the housing and from the adjacent recess in the end wall, it is not possible to block the flow of air into or out of the housing by accidentally locating an end of the light source against a wall or by dropping a towel or the like over it. The combination of the handle and the V-shaped recess assures excellent access to open space both for introducing and for ejecting cooling air.

Obviously, minor changes may be made in the form and construction of this invention without departing from its spirit. Thus, it is not desired to confine the invention to the exact form shown and described, but it is desired to include all such as properly come within the scope claimed.

The invention having been thus described, what is claimed as new and desired to secure by Letters Patent is:

1. Light source comprising:
   (a) a box-like housing having a front wall and two opposed end walls, defining an interior space,
   (b) a venting screen on each of the said end walls,
   (c) a fan mounted in the interior space to provide for air flow through the venting screens,
   (d) a lamp assembly mounted in the interior space, and
   (e) a connector formed on one of the said walls for engagement with a fibre optic cable, wherein each end wall of the housing is provided with an indentation on the surface of which is located said venting screen, and wherein a handle bar extends across each indentation to facilitate the carrying of the housing and to prevent the venting screens from being blocked.

2. Light source as recited in claim 1, wherein the connector includes a shutter to close a primary aperture in the wall when there is no engagement with a fibre optic cable.

3. Light source as recited in claim 2, wherein the shutter is mounted in guides which permit vertical sliding movement, wherein the shutter is formed with a secondary aperture that is non-coextensive with the primary aperture when the shutter is in a lower position and co-extensive with the primary aperture when the shutter is in an upper position.

4. Light source as recited in claim 1, wherein the lamp assembly includes two lamps and means for moving the lamps from a first position in which one lamp is in alignment with the connector to a second position in which the other lamp is in alignment with the connector.

5. Light source as recited in claim 4, wherein the said means for moving includes a platform on which the lamps are mounted and which is movable to carry the lamps from the first position to the second position, and wherein an actuating rod is attached to the platform and extends externally of the housing.

6. Light source as recited in claim 5, wherein the rod is provided with a flat vertical surface that bears warning indicia and which is exposed when the lamps are in the said second position.

7. Light source as recited in claim 5, wherein the platform is connected to a switching apparatus which is actuated by movement of the platform between the said first and second positions, and which energizes one lamp or the other only at the termination of the movement at one end or the other.

* * * * *